US011326201B2

(12) United States Patent
Geng et al.

(10) Patent No.: US 11,326,201 B2
(45) Date of Patent: May 10, 2022

(54) METHOD FOR REMOVING NON-TARGET RNA FROM RNA SAMPLE

(71) Applicant: BEIJING TRANSGEN BIOTECH CO., LTD., Beijing (CN)

(72) Inventors: Liang Geng, Beijing (CN); Wen Xin, Beijing (CN)

(73) Assignee: BEIJING TRANSGEN BIOTECH CO., LTD., Beijing (CN)

( * ) Notice: Subject to any disclaimer, the term of this patent is extended or adjusted under 35 U.S.C. 154(b) by 261 days.

(21) Appl. No.: 16/606,944

(22) PCT Filed: Apr. 25, 2018

(86) PCT No.: PCT/CN2018/084323
§ 371 (c)(1),
(2) Date: Oct. 21, 2019

(87) PCT Pub. No.: WO2018/196763
PCT Pub. Date: Nov. 1, 2018

(65) Prior Publication Data
US 2020/0277652 A1 Sep. 3, 2020

(30) Foreign Application Priority Data
Apr. 28, 2017 (CN) .......................... 201710290992.X (51) Int. Cl.
*C12Q 1/6806* (2018.01)
*C12Q 1/6876* (2018.01)

(52) U.S. Cl.
CPC ......... *C12Q 1/6806* (2013.01); *C12Q 1/6876* (2013.01); *C12Q 2521/319* (2013.01); *C12Q 2525/191* (2013.01)

(58) Field of Classification Search
None
See application file for complete search history.

(56) References Cited

U.S. PATENT DOCUMENTS

2015/0284716 A1* 10/2015 Corey ................. C12Q 1/6804
506/26

OTHER PUBLICATIONS

Archer, S.K et al., Selective and flexible depletion of problematic sequences from RNA-seq libraries at the cDNA stage, BMC Genomics, vol. 15:401, pp. 1-9 (Year: 2014).*

* cited by examiner

*Primary Examiner* — Teresa E Strzelecka
(74) *Attorney, Agent, or Firm* — Paratus Law Group, PLLC (57) ABSTRACT

The present disclosure relates to a method for removing a non-target RNA from an RNA sample, including: performing reverse transcription on an RNA sample by using a reverse transcription primer, and removing an RNA template, to obtain a non-target first-strand cDNA and a target first-strand cDNA; hybridizing the non-target first-strand cDNA with a specific probe to obtain a non-target first-strand cDNA-probe complex; and digesting the non-target first-strand cDNA-probe complex by using a duplex-specific nuclease to obtain the target first-strand cDNA. The non-target first-strand cDNA-probe complex can be further extended to obtain a double-stranded DNA region that can be completely digested by the duplex-specific nuclease, then the duplex-specific nuclease is added for digestion. The present disclosure provides for simplicity, flexibility, and low costs, and can eliminate the impact of the non-target RNA on the downstream experiments, thereby having great and profound significance for research in the field of transcriptomics and RNA sequencing.

7 Claims, 4 Drawing Sheets

Specification includes a Sequence Listing.

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: 18S rRNA F

<400> SEQUENCE: 1
ggccctgtaa ttggaatgag tc                                      22

<210> SEQ ID NO 2
<211> LENGTH: 21
<212> TYPE: DNA
<213> ORGANISM: Artificial Sequence
<220> FEATURE:
<223> OTHER INFORMATION: 18S rRNA R

<400> SEQUENCE: 2
ccaagatcca actacgagct t                                       21

<210> SEQ ID NO 3
<211> LENGTH: 21
<212> TYPE: DNA
<213> ORGANISM: Artificial Sequence
<220> FEATURE:
<223> OTHER INFORMATION: GAPDH F

<400> SEQUENCE: 3
tcctgcacca ccaactgctt a                                       21

<210> SEQ ID NO 4
<211> LENGTH: 21
<212> TYPE: DNA
<213> ORGANISM: Artificial Sequence
<220> FEATURE:
<223> OTHER INFORMATION: GAPDH R

<400> SEQUENCE: 4
aggggccatc cacagtcttc t                                       21

<210> SEQ ID NO 5
<211> LENGTH: 50
<212> TYPE: DNA
<213> ORGANISM: Artificial Sequence
<220> FEATURE:
<223> OTHER INFORMATION: 18S rRNA Probe 1

<400> SEQUENCE: 5
taatgatcct tccgcaggtt cacctacgga aaccttgtta cgactttac          50

<210> SEQ ID NO 6
<211> LENGTH: 50
<212> TYPE: DNA
<213> ORGANISM: Artificial Sequence

```
<220> FEATURE:
<223> OTHER INFORMATION: 18S rRNA Probe 2

<400> SEQUENCE: 6
ttcctctaga tagtcaagtt cgaccgtctt ctcagcgctc cgccagggcc           50

<210> SEQ ID NO 7
<211> LENGTH: 50
<212> TYPE: DNA
<213> ORGANISM: Artificial Sequence
<220> FEATURE:
<223> OTHER INFORMATION: 18S rRNA Probe 3

<400> SEQUENCE: 7
gtgggccgac cccggcgggg ccgatccgag ggcctcacta aaccatccaa           50

<210> SEQ ID NO 8
<211> LENGTH: 50
<212> TYPE: DNA
<213> ORGANISM: Artificial Sequence
<220> FEATURE:
<223> OTHER INFORMATION: 18S rRNA Probe 4

<400> SEQUENCE: 8
tcggtagtag cgacgggcgg tgtgtacaaa gggcagggac ttaatcaacg           50

<210> SEQ ID NO 9
<211> LENGTH: 50
<212> TYPE: DNA
<213> ORGANISM: Artificial Sequence
<220> FEATURE:
<223> OTHER INFORMATION: 18S rRNA Probe 5

<400> SEQUENCE: 9
caagcttatg acccgcactt actcgggaat tccctcgttc atggggaata           50

<210> SEQ ID NO 10
<211> LENGTH: 50
<212> TYPE: DNA
<213> ORGANISM: Artificial Sequence
<220> FEATURE:
<223> OTHER INFORMATION: 18S rRNA Probe 6

<400> SEQUENCE: 10
attgcaatcc ccgatcccca tcacgaatgg ggttcaacgg gttacccgcg           50

<210> SEQ ID NO 11
<211> LENGTH: 21
<212> TYPE: DNA
<213> ORGANISM: Artificial Sequence
<220> FEATURE:
<221> NAME/KEY: misc_feature
<222> LOCATION: 16-21
<223> OTHER INFORMATION: Adapter 1-Random Primer; n is a or g or c or
      t/u

<400> SEQUENCE: 11
gtctcgtggg ctcggnnnnn n                                          21

<210> SEQ ID NO 12
<211> LENGTH: 8
<212> TYPE: DNA
<213> ORGANISM: Artificial Sequence
<220> FEATURE:
<223> OTHER INFORMATION: 18S rRNA Probe 7

<400> SEQUENCE: 12
```

```
ggttcacc                                                                8

<210> SEQ ID NO 13
<211> LENGTH: 12
<212> TYPE: DNA
<213> ORGANISM: Artificial Sequence
<220> FEATURE:
<223> OTHER INFORMATION: 18S rRNA Probe 8

<400> SEQUENCE: 13
ggttcgtcta cg                                                          12

<210> SEQ ID NO 14
<211> LENGTH: 12
<212> TYPE: DNA
<213> ORGANISM: Artificial Sequence
<220> FEATURE:
<223> OTHER INFORMATION: 18S rRNA Probe 9

<400> SEQUENCE: 14
ggttcaccta cg                                                          12
```

METHOD FOR REMOVING NON-TARGET RNA FROM RNA SAMPLE

CROSS REFERENCE TO PRIOR APPLICATION

This application is a National Stage Patent Application of PCT International Patent Application No. PCT/CN2018/084323 (filed on Apr. 25, 2018) under 35 U.S.C. § 371, which claims priority to Chinese Patent Application No. 201710290992.X (filed on Apr. 28, 2017), which are all hereby incorporated by reference in their entirety.

REFERENCE TO A SEQUENCE LISTING SUBMITTED VIA EFS-WEB

The content of the ASCII text file of the sequence listing named "2020-05-07_13-506-0002_SequenceListing", which is 2.8 kb in size, was created on May 6, 2020 and electronically submitted via EFS-Web on May 7, 2020, is incorporated herein by reference in its entirety.

FIELD OF THE INVENTION

The present invention relates to the field of molecular biology, transcriptomics, and RNA sequencing, and in particular to a method for removing a non-target RNA from an RNA sample.

BACKGROUND OF THE INVENTION

With the advent of the post-genome era, the transcriptomics research, which is a powerful tool, becomes increasingly important in current life science research. The transcriptomics research can help people deeply understand the structure of genes, and reveal the expression situation of genes in specific conditions and the regulation mechanism of organisms for responses to external environment changes. Additionally, the vigorous development of the next-generation sequencing technology, especially the advancement of the RNA sequencing technology, also rapidly promotes the wide application of the transcriptomics research. However, the biggest challenge which the RNA sequencing technology faces currently is low abundance of the target RNA in the total RNA. For example, the mRNA usually accounts for only 1-5% of the total RNA, and most of the total RNA are ribosomal RNA (rRNA) and transfer RNA (tRNA), which are generally not required by researchers and may cause consumption of huge amounts of sequencing resources if not removed. Therefore, the scholars need to remove the non-target RNA from the total RNA sample during the research, and then perform sequencing and downstream bioinformatics analysis works.

In recent years, science researchers have developed various methods to remove the non-target RNA represented by the rRNA. These methods design a removal means by using differences between different RNAs in all aspects, for example, the size, the sequence feature, the 5' phosphate group, the secondary structure, the abundance, and the like all can be used as bases for the removal methods. In addition, there are also several commercial kits which can be used to remove the non-target RNA. It should be first noted that, the mRNA of eukaryotes has a poly(A) tail structure, and thus is easy to be enriched and purified by using poly(T) primers to remove other RNAs, or the cDNA can be directly synthesized by using poly(T) primers. However, the mRNA of prokaryotes does not have such a structure, so removal of the non-target RNA from the total RNA of prokaryotes is more technically difficult. Therefore, all the RNA removal methods described in detail below are methods universally applicable to both the prokaryotes and the eukaryotes.

From the view of techniques, these methods can be classified into three categories: performing the RNA removal step before the cDNA synthesis, simultaneously performing the RNA removal and the cDNA synthesis, and performing the RNA removal step after the cDNA synthesis. The two most important points for making a choice among these methods are removal efficiency and preference for information carried by the RNA during the removal process. Certainly, the most ideal method is to remove as much of the non-target RNA as possible while the desired RNA is retained as much as possible. However, any of the methods has respective advantages, limitations, and possible preferences. These methods are sequentially introduced below.

1. Gel Electrophoresis for Selecting RNAs of Different Sizes

The intact rRNA presents a single band during the gel electrophoresis, so the non-ribosomal RNA between the rRNA bands can be recovered after the electrophoresis (McGrath K C, Thomas-Hall S R, Cheng C T, Leo L, Alexa A, Schmidt S, et al. Isolation and analysis of mRNA from environmental microbial communities. J Microbiol Methods 2008; 75(2):172-6.). Although this recovery method can obtain relatively enriched mRNA, the disadvantages thereof are obvious: the fragmented rRNA and the rRNA precursor are not removed because the sizes thereof are inconsistent with that of the mature rRNA; and the target RNA having a size close to that of the rRNA is removed. In addition, a relatively large initial RNA sample amount and Rnase contamination which is easy to occur during the operation are limitations of this method.

2. Denaturing High Performance Liquid Chromatographic Technique for RNA Separation Physical separation of an RNA can also be implemented by means of the chromatographic technique. The RNA size, the strength of binding to a matrix, and the ion condition of an eluent are important bases for the separation. Some scholars have achieved rapid separation of the rRNA and mRNA from a *Corynebacterium* RNA sample by means of said principle (Castro T L P, Seyffert N, Ramos R T J, Barbosa S, Carvalho R, Pinto A C, et al. Ion Torrent-based transcriptional assessment of a *Corynebacterium pseudotuberculosis* equi strain reveals denaturing high-performance liquid chromatography a promising rRNA depletion method. Microbial Biotechnol 2013; 6(2):168-77.). However, this method also requires a relatively large amount of initial RNA samples, and the wide application thereof needs to be further tested.

3. Exonuclease Degradation Technique Dependent on the 5' Phosphate Group

Epicentre has developed a kit for degrading the rRNA by means of a specific enzymolysis reaction (mRNA-ONLY Prokaryotic mRNA Isolation kit), and the exonuclease used in the kit can selectively degrade an RNA having a 5'-end monophosphate group without degrading an RNA having a 5'-end triphosphate or hydroxyl group. The mature rRNA, which is obtained by means of transcription of a single precursor rRNA, has 5'-end monophosphate and thus can be selectively degraded by the enzyme. The mRNA has a 5'-end triphosphate cap structure and thus can resist degradation from the enzyme. This method uses the general characteristics of different RNA molecular structures for distinguishing and has a wide application range. However, removal efficiency and fidelity of this method are significantly affected by partial degradation of the mRNA in the sample (He S, Wurtzel O, Singh K, Froula J L, Yilmaz S, Tringe S G, et al. Validation of two ribosomal RNA removal methods for microbial metatranscriptomics. Nat Methods 2010; 7(10):807-12.). In particular, in bacteria and archaea, the mRNA half-life is extremely short, and the degradation usually starts after a few minutes of transcription (Rauhut R, Klug G. mRNA degradation in bacteria. FEMS Microbiol Rev 1999; 23(3):353-70.). Therefore, if this kit is used, these partially degraded mRNA fragments having 5'-end monophosphate will be lost.

4. RNaseH and DNaseI Digestion Technique

Another rRNA enzymolysis technique uses the ability of RNaseH to specifically degrade the RNA in DNA:RNA hybrid molecules without degrading RNA single strands (Hausen P, Stein H, Ribonuclease H. An enzyme degrading the RNA moiety of DNA-RNA hybrids. Eur J Biochem/FEBS 1970; 14(2):278-83). In this method, the total RNA is first hybridized or reverse transcribed by using a series of specific primer mixtures for the rRNA, and then RNaseH is added to degrade the rRNA in the DNA:RNA hybrid duplex, and then DNaseI is added to degrade the residual DNA. John Morlan used this principle to design short antisense DNA probes (50-80 bp) for 5S, 18S, and 28S rRNAs of the human/rat/mouse. After hybridizing these probes with the human RNA and subsequent treatment using RNase H and DNase I, and 98% of the rRNA can be removed by means of this method (John D. Morlan, Kunbin Qu, Dominick V. Sinicropi. Selective Depletion of rRNA Enable Whole Transcriptome Profiling of Archival Fixed Tissue. PLOS One, 2012 vol 7, e42882).

The above described digestion technique based on RNaseH and DNaseI has the following extremely obvious disadvantages: first, since the used primers are designed for the target RNA, the possibility of these primers not hybridizing with the non-target RNA is extremely low, so it is highly probable that a part of the non-target RNA is present in the final target RNA; second, the target RNA is obtained after a series of treatments with Rnase H, DNase, etc., and the RNA is extremely easy to be contaminated and degraded, so the target RNA is more likely to be degraded if there are more removal steps.

5. Subtractive Hybridization Technique Using Specific Probes

Subtractive hybridization uses the antisense sequence of the rRNA as a specific probe, and the hybrid molecules thus can be removed from the solution after the rRNA is hybridized with the probe bound to a microsphere or magnetic bead (Pang X, Zhou D S, Song Y J, Pei D, Wang J, Guo Z, et al. Bacterial mRNA purification by magnetic capture-hybridization method. Microbiol Immunol 2004; 48(2):91-6.). This method is currently the most widely used technique, probably due to use of this technique in various commercial kits. For example, the MICROBExpress kit of Ambion uses two continuous steps of hybridization to capture the rRNA on magnetic beads. However, there are specific species limitations in use of the kit, where the kit is inapplicable to all archaeal samples; and limited by the type and amount of the used probe, the kit requires high integrity of the RNA sample, so the degraded rRNA often cannot be effectively removed due to loss of hybridization sites. In addition, the Ribo-Zero kit recently developed by Epicentre uses a specific probe coupled with biotin, so that the rRNA can be removed by using corresponding streptavidin-coated affinity chromatographic magnetic beads after hybridizing with the probe (Sooknanan R, Pease J, Doyle K. Novel methods for rRNA removal and directional, ligation-free RNA-seq library preparation. Nat Methods Appl Notes 2010; 7(10).).

Compared to the MICROBExpress kit, this kit can provide a broader rRNA removal range, probably due to use of more proprietary probes therein. However, this method requires a larger initial RNA sample amount, otherwise the removal efficiency may be significantly limited.

Use of either of the above-described kits is limited by selection of a probe. Therefore, there is a probe design method for sample-based specific removal, and in fact, the method is invented even earlier than the commercial kits. Recently, some scholars have developed a species-specific rRNA elimination system (Li S-K, Zhou J-W, Yim A K-Y, Leung A K Y, Tsui S K W, Chan T F, et al. Organism-Specific rRNA capture system for application in next-generation sequencing. PLoS One 2013; 8(9):e74286.), which is applicable to a single species or simple community. For complex communities, some scholars have developed corresponding rRNA removal schemes (Stewart F J, Ottesen E A, DeLong E F. Development and quantitative analyses of a universal rRNA-subtraction protocol for microbial metatranscriptomics. ISME J 2010; 4(7):896-907.). Although obtaining relatively successful results in a certain range, these methods yet have not been widely promoted, mainly due to larger time consumption during the process and a requirement of more sophisticated design and optimization techniques in comparison with the commercial kits.

6. Removal Method Based on a Preference for mRNA 3'-End Polyadenylation Relative to rRNA Some scholars find that the mRNA instead of the rRNA of *Escherichia coli* can be selectively polyadenylated by using a poly(A) polymerase derived from the yeast, and then speculate that when the rRNA is bound to the ribosomal protein, the 3'-end polyadenylation is subject to steric hindrance (Amara R R, Vijaya S. Specific polyadenylation and purification of total messenger RNA from *Escherichia coli*. Nucleic Acids Res 1997; 25(17):3465-70.). Based on this phenomenon, some scholars combines this method with the Oligo(dT) affinity chromatographic purification technique to achieve mRNA enrichment (Wendisch V F, Zimmer D P, Khodursky A, Peter B, Cozzarelli N, Kustu S. Isolation of *Escherichia coli* mRNA and comparison of expression using mRNA and total RNA on DNA microarrays. Anal Biochem 2001; 290(2):205-13.). Some other scholars add poly(A) to the mRNA by means of this method and then specifically synthesize the cDNA by using an Oligo(dT) primer (Frias-Lopez J, Shi Y, Tyson G W, Coleman M L, Schuster S C, Chisholm S W, et al. Microbial community gene expression in ocean surface waters. Proc Natl Acad Sci USA 2008; 105(10):3805-10.). According to the authors, the mRNA enrichment effect of this method is not only due to the preference of polyadenylation, but also to the hindrance to synthesis by the secondary structure of the rRNA. However, some scholars point out the limitations of the Oligo(dT) primers to the 5'-end, especially long transcripts, in comparison with random primers in use of this method (Wilhelm B T, Landry J R. RNA-Seq-quantitative measurement of expression through massively parallel RNA-sequencing. Methods 2009; 48(3):249-57.).

7. Selective Primer Binding During cDNA Synthesis

In all of the above-described methods, the non-target RNA is removed before the cDNA synthesis, and random primers are used to achieve non-preferred transcriptome coverage during synthesis. In fact, selective cDNA synthesis for a specific RNA can be achieved by selecting a subset of sequences that are not completely random from the completely random primers to treat different RNA molecules differentially (Gonzalez J M, Robb F T. Counterselection of prokaryotic ribosomal RNA during reverse transcription using non-random hexameric oligonucleotides. J Microbiol Methods 2007; 71(3):288-91.). This method is easy to operate in the laboratory and does not require a relatively large amount of initial RNA samples. In order to obtain a highly specific selective primer, a computer-based design is indispensable, and some scholars have made exploratory work in this aspect (Armour C D, Castle J C, Chen R, Babak T, Loerch P, Jackson S, et al. Digital transcriptome profiling using selective hexamer priming for cDNA synthesis. Nat Methods 2009; 6(9):647-9.). In addition, NuGEN has developed kits of selective primers for different species (Ovation Prokaryotic RNA-Seq System). However, the actual performance thereof is not satisfactory, and there are great differences for different species. Compared to the above-described several kits developed on the basis of other principles, the specificity thereof is ranked merely downstream.

8. cDNA Library Standardization

The rRNA can also be removed after the cDNA synthesis (Ko M S H. An "equalized cDNA library" by the reassociation of short double-stranded cDNAs. Nucleic Acids Res 1990; 18(19):5705-11.). In this method, the double-stranded cDNA is first denatured at high temperature and then reannealed at low temperature. Since the reannealing rate of the cDNA is proportional to the square of the concentration of the cDNA, the cDNA obtained by transcription of an RNA (such as the rRNA, or the tRNA) of higher concentration is annealed before the cDNA obtained by transcription of an RNA (such as the mRNA) of lower concentration is annealed, i.e., the double strands thereof are formed earlier. Therefore, by controlling appropriate time points for annealing termination, the cDNAs formed by RNAs of different sources can be respectively in different states of single-stranded and double-stranded states; in this case, the duplex-specific nuclease (DSN) is used for digestion or physical separation is performed by means of chromatography, so as to remove the non-target RNA. Because the method is operated after the cDNA library is constructed, the amount of required initial RNA samples can be reduced to below the microgram level. However, this method also has significant limitations, impacts of the concentration, GC content, and mRNA abundance are obvious, and for community RNA samples, the difference in RNA concentration between different species is also one of the serious influencing factors, causing different RNAs incapable of being effectively separated.

The various methods described above each have respective limitations, so some scholars have tried to combine different methods to improve the removal efficiency (Poretsky R S, Hewson I, Sun S, Allen A E, Zehr J P, Moran M A. Comparative day/night metatranscriptomic analysis of microbial communities in the North Pacific subtropical gyre. Environ Microbiol 2009; 11(6):1358-75. Peano C, Pietrelli A, Consolandi C, Rossi E, Petiti L, Tagliabue L, et al. An efficient rRNA removal method for RNA sequencing in GC-rich bacteria. Microbial Inform Experiment 2013; 3(1): 1.). However, in some cases, these methods may improve the removal efficiency while producing a higher preference; and added steps such as processing and purification may bring more material loss and higher contamination probability. Therefore, cautiousness should be involved in choosing a combination of multiple methods.

Given the above, enriching a required RNA and removing a non-target RNA from the total RNA sample are crucial steps in transcriptomics and RNA sequencing research. The existing various removal methods each have respective limitations, which are reflected in aspects such as the requirements of the sample, the removal efficiency, and the preference. Evaluation tests for these methods and development of new methods are research contents attracting much attention currently. As far as the existing methods are concerned, there is no technique that can completely remove the non-target RNAs, and these residual RNAs can be amplified during subsequent library construction and amplification processes, thereby generating useless information, affecting subsequent analysis work. Therefore, there is an urgent need for a technique that can remove all the non-target RNAs before the library construction is completed, without worrying about the impacts of residues thereof on downstream work.

SUMMARY OF THE INVENTION

The objective of the present invention is to provide a method for removing a non-target RNA from an RNA sample, the method being capable of completely removing the non-target RNA so as to avoid an impact thereof on downstream tests.

In order to achieve the above-described objective, the present invention adopts the following technical solutions.

The present invention provides a method for removing a non-target RNA from an RNA sample, comprising the following steps: (1) performing reverse transcription on an RNA sample by means of a reverse transcription primer, and removing an RNA template, to obtain a non-target first-strand cDNA and a target first-strand cDNA; (2) hybridizing the non-target first-strand cDNA with a specific probe to obtain a non-target first-strand cDNA-probe complex; and (3) digesting the non-target first-strand cDNA-probe complex by means of a duplex-specific nuclease to obtain the target first-strand cDNA.

Figure 1:
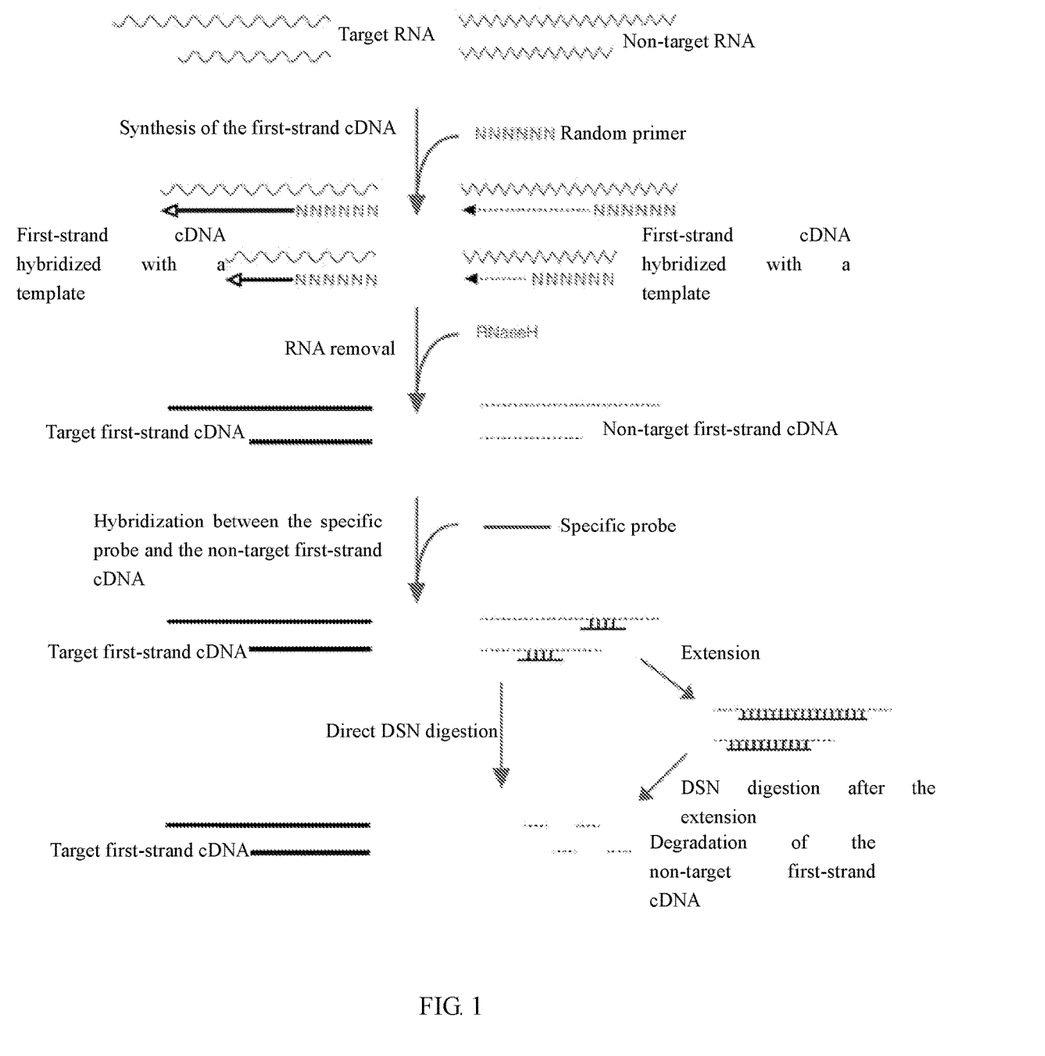
FIG. 1 illustrates a schematic diagram of a principle of the present invention.

In a preferred embodiment of the present invention, the non-target first-strand cDNA-probe complex obtained in step (2) is further extended to obtain a completely complementary non-target first-strand cDNA-probe complex that can be completely digested by the duplex-specific nuclease (DSN enzyme) and has a sufficient length, and then the duplex-specific nuclease is used for digestion (see FIG. 1).

Further, in the present invention, the reverse transcription primer used for synthesizing the first-strand cDNA is a random primer having a 5'-end provided with a first adaptor sequence or no first adaptor sequence, the random primer being capable of enabling the reverse transcription by binding to any RNA component in the RNA sample.

In the present invention, when the random primer having a 5'-end provided with a first adaptor sequence is used, a first adaptor can be introduced to a 5'-end of the synthesized first-strand cDNA, and after the RNA template is removed by means of RNase H, a second adaptor is added to a 3'-end of the first-strand cDNA by means of an RNA ligase, specifically comprising the following steps: (1) performing reverse transcription on an RNA sample by means of the random primer having a 5'-end provided with a first adaptor, removing the RNA template, and adding the second adaptor to the 3'-end of the first-strand cDNA, to obtain non-target and target first-strand cDNAs having two ends provided with adaptor sequences; (2) hybridizing the non-target first-strand cDNA having two ends provided with adaptor sequences with a specific probe to obtain a non-target first-strand cDNA-probe complex having two ends provided with adaptor sequences; and (3) digesting the non-target first-strand cDNA-probe complex by means of a duplex-specific nuclease to obtain the target first-strand cDNA having two ends provided with adaptor sequences.

Further, the second adaptor may be first added to the 3'-end of the first-strand cDNA by means of the RNA ligase, and then the RNA template is removed by means of the RNase H, specifically comprising the following steps: (1) performing reverse transcription on an RNA sample by means of the random primer having a 5'-end provided with a first adaptor, adding the second adaptor to the 3'-end of the first-strand cDNA, and removing the RNA template, to obtain non-target and target first-strand cDNAs having two ends provided with adaptor sequences; (2) hybridizing the non-target first-strand cDNA having two ends provided with adaptor sequences with a specific probe to obtain a non-target first-strand cDNA-probe complex having two ends provided with adaptor sequences; and (3) digesting the non-target first-strand cDNA-probe complex by means of a duplex-specific nuclease to obtain the target first-strand cDNA having two ends provided with adaptor sequences.

In a preferred embodiment of the present invention, the non-target first-strand cDNA-probe complex having two ends provided with adaptor sequences obtained in step (2) is further extended to obtain a completely complementary non-target first-strand cDNA-probe complex having two ends provided with adaptor sequences that can be completely digested by the duplex-specific nuclease (DSN enzyme) and has a sufficient length, and then the duplex-specific nuclease is used for digestion.

Figure 2:
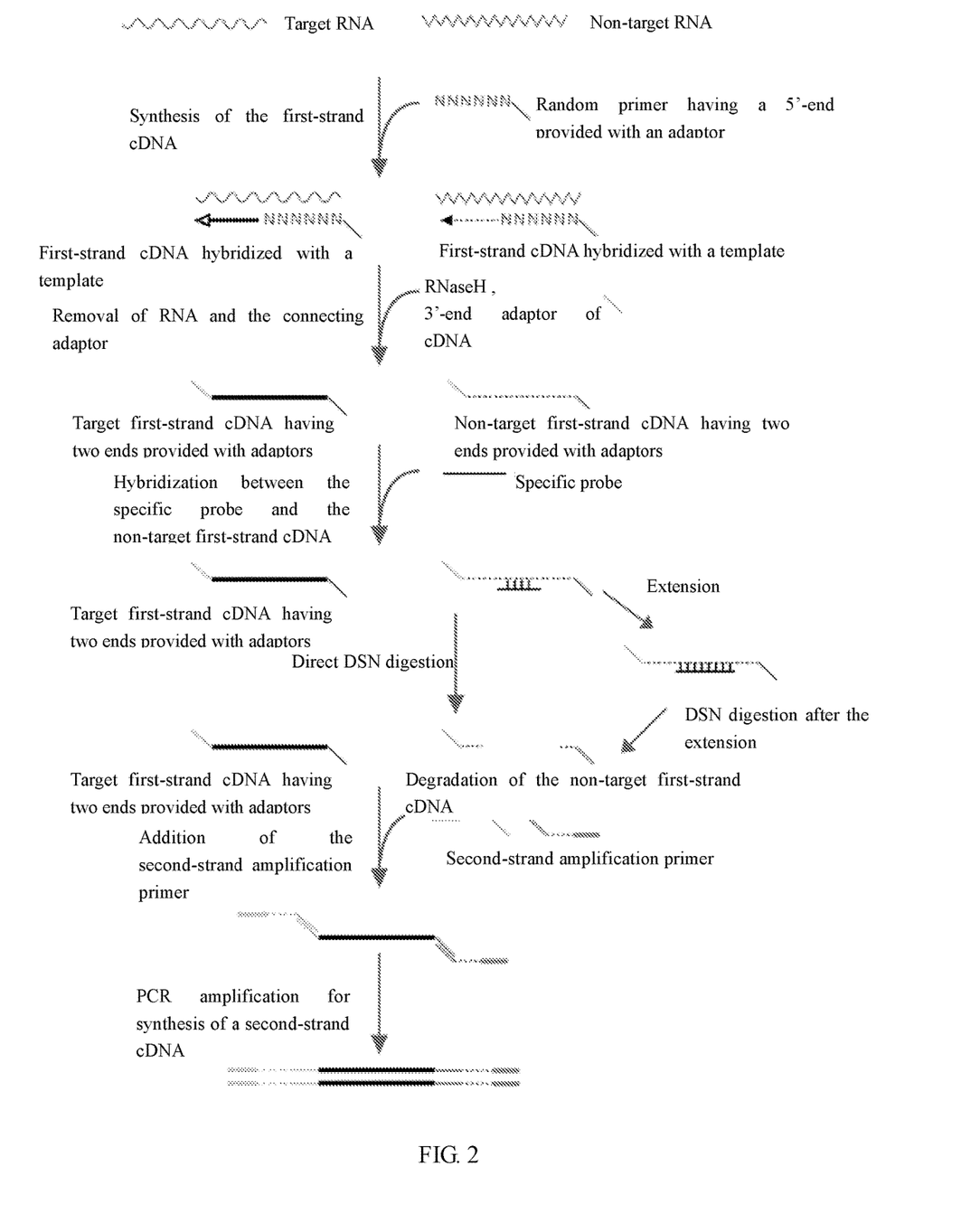
FIG. 2 illustrates a schematic diagram of constructing an RNA next-generation sequencing library according to the present invention.

In the present invention, the target first-strand cDNA sequence having two ends provided with adaptor sequences is obtained by means of the random primer having a 5'-end provided with the first adaptor sequence, without a polymerase chain reaction (PCR), and the cDNA having two ends provided with adaptors are used as a library of the RNA next-generation sequencing. A second-strand cDNA can be synthesized by means of a PCR method, in which case a used PCR primer is complementary to the first and second adaptors at the two ends of the first-strand cDNA. A 5'-end of the PCR primer can be provided with another sequence, so that required sequences are added to the two ends of the cDNA after PCR amplification, thereby satisfying downstream experimental needs, for example, library construction for RNA sequencing (see FIG. 2).

In the present invention, the adaptor sequences at the two ends of the cDNA can be identical or different, specifically selected according to downstream test objectives.

Further, in the present invention, after the non-target first-strand cDNA is degraded, the remaining target first-strand cDNA can be amplified by means of the PCR method for downstream tests, wherein a PCR primer can be a specific primer of a gene to be amplified and designed according to downstream test needs.

In a preferred embodiment of the present invention, the specific probe is a specific probe designed according to a non-target RNA sequence and can be obtained by means of chemical synthesis or other molecular biological methods. The specific probe can be 100% complementary to the first-strand cDNA sequence obtained by means of reverse transcription of the non-target RNA, or can be a partially complementary degenerate basic group, and the basic groups are satisfactory as long as they can be used as primers of double-stranded cDNA synthesis. Specifically, in the present invention, a proportion of the basic groups of the specific probe that are complementary to the first-strand cDNA sequence obtained by means of reverse transcription of the non-target RNA is determined by the DSN enzyme, different DSN enzymes require different lengths, and any specific probe that can hybridize with the first-strand cDNA sequence obtained by means of reverse transcription of the non-target RNA falls within the protection scope of the present invention.

Further, in the present invention, the RNA sample can be any RNA sample, comprising but not limited to a directly extracted RNA, an RNA subject to segmentation breaking, an mRNA enriched by means of the prior art, an RNA from which an rRNA is removed by means of the prior art, and the like.

The non-target RNA can be any RNA component in the RNA sample, comprising but not limited to an rRNA, a tRNA, an mRNA, and the like. Preferably, the non-target RNA is an rRNA. The target RNA can be any RNA component in the RNA sample, comprising but not limited to a coding RNA, a non-coding RNA, and the like.

Further, in the present invention, the non-target first-strand cDNA is a first-strand cDNA obtained by means of reverse transcription of the non-target RNA, and the target first-strand cDNA is a first-strand cDNA obtained by means of reverse transcription of the target RNA.

Further, the duplex-specific nuclease of the present invention can be any nuclease that can specifically degrade a double-stranded DNA without degrading a single-stranded DNA.

Any traditional RNA removal method, whether the step is performed before, during, or after the cDNA synthesis, has respective limitations and cannot achieve 100% removal of the non-target RNA, and there are different degrees of preferences in removal processes. Moreover, these methods are mostly designed for the rRNA and tRNA, and are helpless in some cases where other RNAs need to be removed. Commercial rRNA removal kits are usually only targeted at some samples of a specific species and have high requirements on the sample amount, and the remaining RNA or a degradation product thereof which can be amplified still affects downstream experiments, thereby contaminating subsequent experimental data. The present invention is a technique where the non-target first-strand cDNA-probe complex is formed by binding the specific probe to the first-strand cDNA synthesized by using the non-target RNA, and then the complex is subject to enzymolysis by means of the duplex-specific nuclease, so that the non-target first-strand cDNA cannot be used as a template for PCR amplification, thereby eliminating the impact of the non-target RNA portion in the total RNA sample on the downstream experiments. By appropriately designing a sequence, a length and an amount of the probe by means of bioinformatics means, when information of the RNA sample to be processed is known, any non-target RNA can be selectively removed from any RNA sample while an RNA to be studied is retained.

The present invention has the following beneficial effects:

In the present invention, a local double-stranded DNA region is formed by binding the specific probe to the first-strand cDNA synthesized by using the non-target RNA; then the duplex-specific nuclease (DSN) is used to directly digest the cDNA or digest the cDNA after extending, so that the cDNA is broken and cannot be used as a template for PCR amplification, thereby completely eliminating the impact of the non-target RNA on the downstream experiments. Compared to the traditional method, in the present invention, the non-target RNA or the first-strand cDNA generated thereby does not need to be completely degraded, and the cDNA cannot be used as a template for amplification after being broken. Therefore, the present invention can achieve specific removal efficiency that significantly exceeds any existing method, higher removal strength, and higher fidelity to a desired sequence, and is not limited by species or samples, that is, being capable of specifically removing or retaining any component in any RNA sample.

According to the method of the present invention, adaptor sequences can be introduced to two ends of the first-strand cDNA in synthesis of the first-strand cDNA, any desired sequence can be flexibly and directly added to the end of the cDNA, or any desired sequence can be flexibly and directly added to the end of the cDNA when the second-strand cDNA is synthesized by means of the PCR method, so as to achieve different downstream experimental objectives, for example, library construction for RNA next-generation sequencing.

The method of the present invention has simple operations, flexibility, and low costs, and has great and profound significance for research in the field of transcriptomics and RNA sequencing.

BRIEF DESCRIPTION OF THE DRAWINGS

The specific embodiments of the present invention are further described in detail below with reference to the drawings.

DETAILED DESCRIPTION OF THE PREFERRED EMBODIMENTS

In order to more clearly describe the present invention, the present invention is further described below with reference to the preferred embodiments and the drawings. The similar components in the drawings are represented by the same reference number. A person skilled in the art should understand that the following specific description content is for description instead of for limitation, and the protection scope of the present invention shall not be limited thereto.

Materials Used in the Examples and Sources Thereof:

EasyPure® RNA Kit, TransScript® First-Strand cDNA Synthesis SuperMix, TransStart® Tip Green qPCRSuperMix, and EasyTaq® DNA Polymerase, Beijing TransGen Biotech Co., Ltd.

RNase H and T4 RNA Ligase I, NEB dsDNase, Thermo Fisher Scientific

Primer synthesis, Life technologies

Example 1 Verification of the Present Invention being Effective in Removing the 18S rRNA from a Total RNA and Retaining the Desired mRNA 1. Preparation of a Human Total RNA The human total RNA is extracted by means of the EasyPure® RNA Kit, using a HeLa cell as a material.

2. Synthesis of Primers and Probes the Following Primers and Probes are Designed According to Human 18S rRNA and GAPDH gene sequences:

```
18S rRNA F:
5'-GGCCCTGTAATTGGAATGAGTC-3' (see SEQ ID No. 1 in
the sequence table)

18S rRNA R:
5'-CCAAGATCCAACTACGAGCTT-3' (see SEQ ID No. 2 in
the sequence table)

GAPDH F:
5'-TCCTGCACCACCAACTGCTTA-3'(see SEQ ID No. 3 in the
sequence table)

GAPDH R:
5'-AGGGGCCATCCACAGTCTTCT-3' (see SEQ ID No. 4 in
the sequence table)
All the above four primers are dissolved to 10 μM
by using ddH2O.

18S rRNA Probe 1:
5'-TAATGATCCTTCCGCAGGTTCACCTACGGAAACCTTGTTACGACTTTT
AC-3' (see SEQ ID No. 5 in the sequence table)

18S rRNA Probe 2:
5'-TTCCTCTAGATAGTCAAGTTCGACCGTCTTCTCAGCGCTCCGCCAGGG
CC-3' (see SEQ ID No. 6 in the sequence table)

18S rRNA Probe 3:
5'-GTGGGCCGACCCCGGCGGGGCCGATCCGAGGGCCTCACTAAACCATCC
AA-3' (see SEQ ID No. 7 in the sequence table)

18S rRNA Probe 4:
5'-TCGGTAGTAGCGACGGGCGGTGTGTACAAAGGGCAGGGACTTAATCAA
CG-3' (see SEQ ID No. 8 in the sequence table)

18S rRNA Probe 5:
5'-CAAGCTTATGACCCGCACTTACTCGGGAATTCCCTCGTTCATGGGGAA
TA-3'(see SEQ ID No. 9 in the sequence table)

18S rRNA Probe 6:
5'-ATTGCAATCCCCGATCCCCATCACGAATGGGGTTCAACGGGTTACCCG
CG-3' (see SEQ ID No. 10 in the sequence table)
```

All the above six probes are dissolved to 1 μg/μl by using ddH$_2$O, and then a probe combination 1/2/3 is prepared:

probe combination 1: 18S rRNA Probe 1 probe combination 2: a mixture of 18S rRNA Probe 2 and 18S rRNA Probe 3 mixed in equal proportions probe combination 3: a mixture of 18S rRNA Probe 4, 18S rRNA Probe 5, and 18S rRNA Probe 6 mixed in equal proportions

```
Adaptor 1-Random Primer:
5'-GTCTCGTGGGCTCGGNNNNNN-3'(see SEQ ID No. 11 in
the sequence table)
```

This primer is dissolved to 0.1 μg/μl by using ddH$_2$O.

3. Synthesis of a First-Strand cDNA

Reverse transcription is performed on the total RNA extracted in step 1, using the Adapter 1-Random Primer and TransScript® First-Strand cDNA Synthesis SuperMix. Reaction systems are as follows:

| | |
|---|---|
| Total RNA | 200 ng |
| Adapter 1-Random Primer 1 μl | |
| 2 × TS Reaction Mix | 10 μl |
| TransScript ® RT/RI Enzyme Mix | 1 μl |
| RNase-free Water | to 20 μl |

Reaction conditions are as follows: incubation for 10 minutes at 25° C., incubation for 30 minutes at 42° C., and heating for 5 seconds at 85° C. for deactivation of the TransScript® RT/RI.

4. RNA Template Digestion

An RNA template binding to the first-strand cDNA is digested by using RNase H. Reaction systems are as follows:

| | |
|---|---|
| Reverse transcription reaction product | 20 μl |
| 10 × RNase H Reaction Buffer | 2.5 μl |
| E. coli RNase H | 1 μl |
| RNase-free Water | to 25 μl |

Reaction conditions are as follows: incubation for 30 minutes at 37° C., and incubation for 20 minutes at 65° C. for deactivation of the E. coli RNase H.

5. Probe Hybridization

Three probe hybridization systems and one control reaction system (the probe is replaced by ddH$_2$O) are prepared:

| | |
|---|---|
| First-strand cDNA | 5 μl |
| ddH$_2$O or probe combination 1/2/3 | 1 μl |
| 500 mM Tris-HCl pH 7.5 | 2 μl |
| ddH$_2$O | to 10 μl |

Reaction conditions are as follows:

| | | |
|---|---|---|
| 95° C. | denaturation | 2 minutes |
| 95° C.→22° C. | hybridization | 0.1 °C./second, about 12 minutes |
| 22° C. | incubation | 5 minutes |

6. Digestion Using Duplex-Specific Nuclease

All the four hybridization reaction systems in the last step are digested by using dsDNase, and reaction systems are as follows:

| | |
|---|---|
| hybridization reaction system | 8 μl |
| 10 × dsDNase Buffer | 1 μl |
| dsDNase | 1 μl |

Reaction conditions are as follows:

incubation for 2 minutes at 37° C., addition of 0.1 μl of 1 M DTT to the system, and incubation for 5 minutes at 55° C. for deactivation of the dsDNase.

7. qPCR Detection for 18S rRNA Removal Efficiency

The four digestion reaction systems in the last step are used as templates, and the first-strand cDNA obtained in step 4 of the same amount is used as a control template, the two pairs of primers 18S rRNA F/R and GAPDH F/R are used for amplification, and qPCR reaction systems are set as follows:

digestion reaction system/first-strand cDNA 1.0 μl/0.4 μl

| | |
|---|---|
| Primer F (10 μM) | 0.4 μl |
| Primer R (10 μM) | 0.4 μl |
| 2 × TransStart ®Tip Green qPCRSuperMix | 10 μl |
| ddH$_2$O | to 20 μl | qPCR reaction conditions are as follows:

| | | |
|---|---|---|
| 94° C. | 30 seconds | |
| 94° C. | 5 seconds | |
| 50-60° C. | 15 seconds | } 45 cycles |
| 72° C. | 10 seconds | |

Melting Curve Phase

Figure 3:
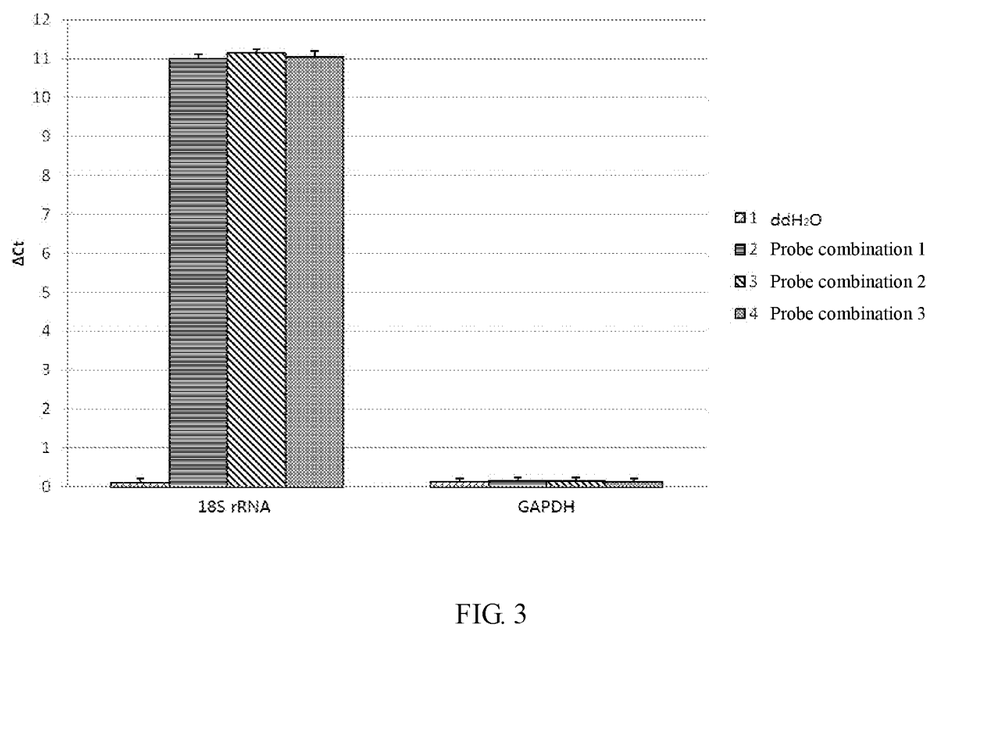
FIG. 3 illustrates qPCR verification results of an RNA subject to different treatments in example 1.

Data of all qPCR Ct values is shown in Table 1 below. Differences between Ct values in the cases of templates treated with different methods in steps 5 and 6 and a Ct value in the case of an untreated template are shown in FIG. 3. It can be seen from Table 1 and FIG. 3 that:

compared to the case of a cDNA template subject to no any treatment, when the 18S rRNA gene is amplified by using a cDNA which is hybridized with each of the three probe combinations and digested by using the dsDNase, the Ct value thereof is delayed by more than 10 cycles, that is, more than 99.9% of the 18S rRNA is not amplified; and compared to the case of an untreated cDNA template, in amplification of the GAPDH gene, the Ct value changes extremely slightly. In addition, compared to the case of an untreated cDNA template, when the cDNA template is hybridized with water that replaces the probe and digested, the Ct value of either of the 18S rRNA and GAPDH genes changes extremely slightly. Therefore, it is verified that the present invention is successful in effectively removing the non-target 18S rRNA from the total RNA.

In addition, the three different probe combinations have comparable removal effects, and all the results are satisfactory, indicating that the sequence, length, and amount of the probe are very flexible in designing of the hybridization probe, and the removal objective can be successfully achieved as long as the probe can bind to the non-target first-strand cDNA to cause a subsequent enzymolysis breakage thereon.

TABLE 1

All the qPCR Ct values in example 1

| | | Template treatment method | | | | |
|---|---|---|---|---|---|---|
| | Gene | Untreated | ddH$_2$O | Probe combination 1 | Probe combination 2 | Probe combination 3 |
| 18S rRNA | Original data of the Ct value | 11.62 | 11.73 | 22.62 | 22.77 | 22.67 |
| | Difference in the Ct value compared to the case of an untreated template | — | 0.11 | 11.00 | 11.15 | 11.05 |

TABLE 1-continued

All the qPCR Ct values in example 1

| | | Template treatment method | | | | |
|---|---|---|---|---|---|---|
| Gene | | Untreated | ddH$_2$O | Probe combination 1 | Probe combination 2 | Probe combination 3 |
| GAPDH | Original data of the Ct value | 17.32 | 17.44 | 17.56 | 17.47 | 17.45 |
| | Difference in the Ct value compared to the case of an untreated template | — | 0.12 | 0.24 | 0.15 | 0.13 |

Example 2 Verification of an Impact of an Effective Length of a Completely Matching Double-Stranded DNA Region Formed after the Hybridization on DSN Degradation Efficiency 1. Preparation of a Human Total RNA The human total RNA is extracted by means of the EasyPure® RNA Kit, using a HeLa cell as a material.

2. Synthesis of Primers and Probes

The following primers and probes are designed:

```
18S rRNA Probe 7:
5'-GGTTCACC-3' (see SEQ ID No. 12 in the sequence
table)

18S rRNA Probe 8:
5'-GGTTCGTCTACG-3' (see SEQ ID No. 13 in the
sequence table)

18S rRNA Probe 9:
5'-GGTTCACCTACG-3' (see SEQ ID No. 14 in the
sequence table)
```

All the above three probes are dissolved to 1 μg/μl by using ddH$_2$O. The three probes have the following differences and relations:

Probe 7: having a length of 8 nt and being completely complementary to the 18S rRNA;

Probe 8: having a length of 12 nt, being partially complementary to the 18S rRNA, and having two mismatched basic groups; and Probe 9: having a length of 12 nt and being completely complementary to the 18S rRNA.

3. Synthesis of a First-Strand cDNA

See step 3 in example 1.

4. RNA Template Digestion

See step 4 in example 1.

5. Probe Hybridization

Three probe hybridization systems and one control reaction system (the probe is replaced by ddH$_2$O) are prepared:

| | |
|---|---|
| First-strand cDNA | 5 μl |
| ddH$_2$O or probe 7/8/9 | 1 μl |
| 500 mM Tris-HCl pH 7.5 | 2 μl |
| ddH$_2$O | to 10 μl |

Reaction conditions are as follows:

| | | |
|---|---|---|
| 95° C. | denaturation | 2 minutes |
| 95° C.→22° C. | hybridization | 0.1 ° C./second, about 12 minutes |
| 22° C. | incubation | 5 minutes |

6. Probe Extension

All the four hybridization reaction systems obtained in step 5 are divided into two halves, one half being directly used for a digestion reaction in the subsequent step 7, and the other half being used for probe extension according to the following reaction system:

| | |
|---|---|
| hybridization reaction system | 5 μl |
| EasyTaq® DNA Polymerase | 0.1 μl |

A reaction condition is as follows:

incubation for 1 minute at 72° C.

7. Digestion Using Duplex-Specific Nuclease

All the four hybridization reaction systems obtained in step 5 and the four extension reaction systems obtained in step 6 are digested by using dsDNase, and reaction systems are as follows:

hybridization/extension reaction system 4 μl

| | |
|---|---|
| 10 × dsDNase Buffer | 1 μl |
| dsDNase | 1 μl |
| ddH$_2$O | to 10 μl |

Reaction conditions are as follows:

incubation for 2 minutes at 37° C., addition of 0.1 μl of 1 M DTT to the system, and incubation for 5 minutes at 55° C. for deactivation of the dsDNase.

8. qPCR Detection for 18S rRNA Removal Efficiency

The eight digestion reaction systems in the last step are used as templates, and the first-strand cDNA obtained in step 4 of the same amount is used as a control template, the two pairs of primers 18S rRNA F/R and GAPDH F/R are used for amplification, and qPCR reaction systems are set as follows:

| | |
|---|---|
| digestion reaction system/first-strand cDNA | 1.0 μl/0.2 μl |
| Primer F (10 μM) | 0.4 μl |
| Primer R (10 μM) | 0.4 μl |
| 2 × TransStart® Tip Green qPCRSuper-Mix | 10 μl |
| ddH$_2$O | to 20 ul | qPCR reaction conditions are as follows:

| | | |
|---|---|---|
| 94° C. | 30 seconds | |
| 94° C. | 5 seconds | |
| 50-60° C. | 15 seconds | } 45 cycles |
| 72° C. | 10 seconds | |

Melting Curve Phase

Figure 4:
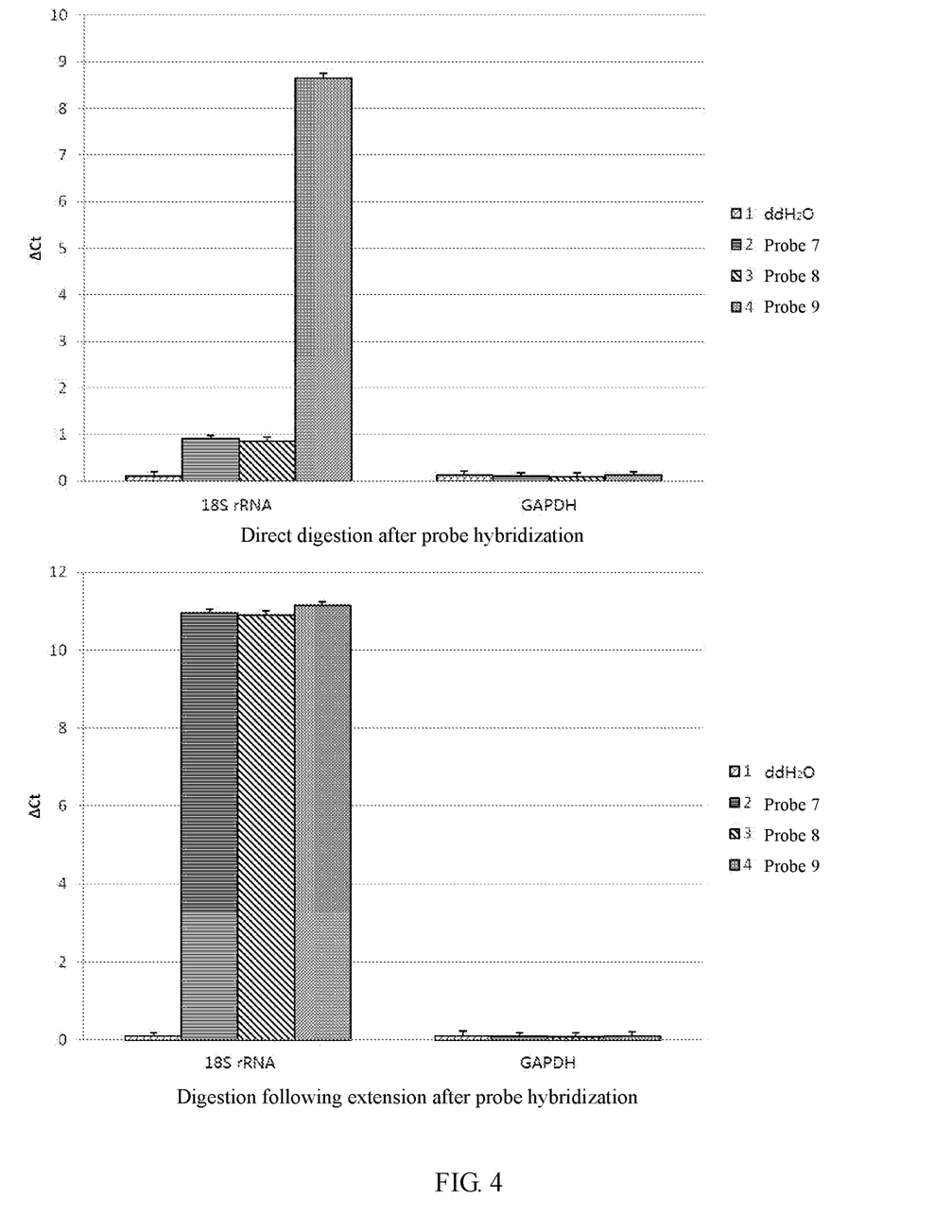
FIG. 4 illustrates qPCR verification results of an RNA subject to different treatments in example 2.

Data of all qPCR Ct values is shown in Table 2 and Table 3 below. Differences between Ct values in the cases of templates treated with different methods in steps 5 to 7 and a Ct value in the case of an untreated template are shown in FIG. 4. It can be seen from Table 2, Table 3, and FIG. 4 that:

when hybridization products are directly digested by using the dsDNase, compared to the case of a cDNA template subject to no any treatment, when the 18S rRNA gene is amplified by using either of the hybridization products of the probe 7 and probe 8, the Ct value thereof does not change significantly, merely comparable to or slightly delayed by a negative control; and the Ct value in the case of the hybridization product of the probe 9 is significantly delayed, that is, most of the 18S rRNA is not amplified. In addition, compared to the case of an untreated cDNA template, when the GAPDH gene is amplified by using any of the different probe hybridization products or the negative control, the Ct value thereof changes slightly.

If the hybridization products are extended before digested, compared to the case of a cDNA template subject to no any treatment, when the 18S rRNA gene is amplified by using each of the hybridization and extension products of the three probes, the Ct value thereof is delayed by more than 10 cycles, that is, more than 99.9% of the 18S rRNA is not amplified; and compared to the case of an untreated cDNA template, in amplification of the GAPDH gene, the Ct value changes extremely slightly.

Therefore, the above-described conclusion verifies that an effective digestion function of the duplex-specific nuclease requires a completely complementary double-stranded DNA region having a sufficient length. In this example, the probe 7 is too short; and the probe 8, although longer than the probe 7, is not completely complementary to the cDNA sequence. Therefore, both of the effects of direct digestion after hybridization are unsatisfactory. Only the probe 9 has a sufficient length and is completely complementary to the cDNA. Therefore, the hybridization product thereof can be directly and effectively degraded by the dsDNase.

However, each of the above three probes generates a completely complementary double-stranded DNA having a sufficient length after further synthesized and extended, and all the extended hybridization products can be effectively degraded by the dsDNase. Therefore, this example verifies that, in the present invention, a relatively short probe or a probe partially matching with a sequence of an RNA to be removed can be used for hybridization, then an extension step is performed, so as to implement successful removal of the non-target RNA by using the DSN. The conclusion further verifies and enhances flexibility in designing of a hybridization probe, and the present invention thus is more practical and has a wider application range.

TABLE 2

All the qPCR Ct values in the case of a template obtained by means of direct digestion after probe hybridization in example 2

| | | Template treatment method | | | | |
|---|---|---|---|---|---|---|
| | Gene | Untreated | ddH$_2$O | Probe 7 | Probe 8 | Probe 9 |
| 18S rRNA | Original data of the Ct value | 11.85 | 11.96 | 12.75 | 12.70 | 20.50 |
| | Difference in the Ct value compared to the case of an untreated template | — | 0.11 | 0.90 | 0.85 | 8.65 |
| GAPDH | Original data of the Ct value | 17.90 | 18.02 | 18.01 | 17.99 | 18.02 |
| | Difference in the Ct value compared to the case of an untreated template | — | 0.12 | 0.11 | 0.09 | 0.12 |

TABLE 3

All the qPCR Ct values in the case of a template obtained by means of digestion following extension after probe hybridization in example 2

| | | Template treatment method | | | | |
|---|---|---|---|---|---|---|
| | Gene | Untreated | ddH$_2$O | Probe 7 | Probe 8 | Probe 9 |
| 18S rRNA | Original data of the Ct value | 11.85 | 11.96 | 22.80 | 22.75 | 23.00 |
| | Difference in the Ct value compared to the case of an untreated template | — | 0.11 | 10.95 | 10.90 | 11.15 |
| GAPDH | Original data of the Ct value | 17.90 | 18.01 | 18.01 | 17.98 | 18.00 |
| | Difference in the Ct value compared to the case of an untreated template | — | 0.11 | 0.11 | 0.08 | 0.10 |

Apparently, the above-described embodiments of the present invention are merely illustrative for clear description of the present invention and are not intended to limit the implementations of the present invention, and those skilled in the art could also make other changes or modifications of different forms on the basis of the above description. Any obvious changes or modifications derived from the technical solutions of the present invention still fall within the protection scope of the present invention.

---

The invention claimed is:

1. A method for removing a non-target RNA from an RNA sample, comprising the following steps: (1) performing reverse transcription on an RNA sample by means of a reverse transcription primer, and removing an RNA template, to obtain a non-target first-strand cDNA and a target first-strand cDNA; (2) hybridizing the non-target first-strand cDNA with a specific probe to obtain a non-target first-strand cDNA-probe complex; further extending the non-target first-strand cDNA-probe complex to obtain a non-target first-strand cDNA-probe complex that can be completely digested by the duplex-specific nuclease; and (3) digesting the non-target first-strand cDNA-probe complex by means of a duplex-specific nuclease to obtain the target first-strand cDNA.

2. The method according to claim 1, wherein the reverse transcription primer is a random primer having a 5'-end provided with an adaptor sequence or no adaptor sequence.

3. A method for removing a non-target RNA from an RNA sample, comprising the following steps:
   (1) performing reverse transcription on an RNA sample by means of a random primer having a 5'-end provided with a first adaptor, removing an RNA template, and adding a second adaptor to a 3'-end of a first-strand cDNA, to obtain non-target and target first-strand cDNAs having two ends provided with adaptor sequences; (2) hybridizing the non-target first-strand cDNA with a specific probe to obtain a non-target first-strand cDNA-probe complex having two ends provided with adaptor sequences; further extending the non-target first-strand cDNA-probe complex having two ends provided with adaptor sequences to obtain a non-target first-strand cDNA-probe complex having two ends provided with adaptor sequences that can be completely digested by the duplex-specific nuclease; and (3) digesting the non-target first-strand cDNA-probe complex by means of a duplex-specific nuclease to obtain the target first-strand cDNA having two ends provided with adaptor sequences.

4. A method for removing a non-target RNA from an RNA sample, comprising the following steps:
   (1) performing reverse transcription on an RNA sample by means of a random primer having a 5'-end provided with a first adaptor, adding a second adaptor to a 3'-end of a first-strand cDNA, and removing an RNA template, to obtain non-target and target first-strand cDNAs having two ends provided with adaptor sequences; (2) hybridizing the non-target first-strand cDNA with a specific probe to obtain a non-target first-strand cDNA-probe complex having two ends provided with adaptor sequences; further extending the non-target first-strand cDNA-probe complex having two ends provided with adaptor sequences to obtain a non-target first-strand cDNA-probe complex having two ends provided with adaptor sequences that can be completely digested by the duplex-specific nuclease; and (3) digesting the non-target first-strand cDNA-probe complex by means of a duplex-specific nuclease to obtain the target first-strand cDNA having two ends provided with adaptor sequences.

5. The method according to claim 1, wherein the specific probe is a specific probe designed according to a non-target RNA sequence and is 100% or partially complementary to a non-target first-strand cDNA sequence.

6. The method according to claim 3, wherein the specific probe is a specific probe designed according to a non-target RNA sequence and is 100% or partially complementary to a non-target first-strand cDNA sequence.

7. The method according to claim 3, wherein the specific probe is a specific probe designed according to a non-target RNA sequence and is 100% or partially complementary to a non-target first-strand cDNA sequence.

* * * * *